United States Patent
AlSaffar

(10) Patent No.: US 9,539,134 B2
(45) Date of Patent: Jan. 10, 2017

(54) ORTHOTIC METHOD AND DEVICE FOR NEWBORN BABIES

(71) Applicant: Abdulreidha Abdulrasoul AlSaffar, Sharg (KW)

(72) Inventor: Abdulreidha Abdulrasoul AlSaffar, Sharg (KW)

(*) Notice: Subject to any disclaimer, the term of this patent is extended or adjusted under 35 U.S.C. 154(b) by 0 days.

(21) Appl. No.: 14/752,959

(22) Filed: Jun. 28, 2015

(65) Prior Publication Data

US 2015/0297386 A1   Oct. 22, 2015

Related U.S. Application Data

(63) Continuation-in-part of application No. 14/178,443, filed on Feb. 12, 2014, now abandoned.

(51) Int. Cl.
*A61F 5/00* (2006.01)
*A61F 5/01* (2006.01)

(52) U.S. Cl.
CPC ............ *A61F 5/0111* (2013.01); *A61F 5/019* (2013.01)

(58) Field of Classification Search
CPC ....... A61F 5/0127; A61F 5/019; A61F 5/0195
USPC ....... 602/27–30; 128/893, 882; 36/140, 142, 36/144, 174, 180, 182, 112
See application file for complete search history.

(56) References Cited

U.S. PATENT DOCUMENTS

| | | |
|---|---|---|
| 3,049,120 A | 8/1962 | Marcus |
| 3,171,407 A * | 3/1965 | Rogers ........................... 602/24 |
| 4,088,129 A | 5/1978 | DiGiulio |
| 4,180,870 A | 1/1980 | Radulovic et al. |
| 4,244,359 A | 1/1981 | Dieterich |
| 4,320,747 A | 3/1982 | Daniell, Jr. |
| 4,608,970 A | 9/1986 | Marck et al. |
| 4,649,906 A | 3/1987 | Spademan |
| 5,002,044 A | 3/1991 | Carter |
| 5,183,036 A | 2/1993 | Spademan |
| 5,308,312 A | 5/1994 | Pomatto et al. |
| 5,385,536 A | 1/1995 | Burkhead et al. |
| 5,421,810 A | 6/1995 | Davis et al. |
| 5,503,621 A | 4/1996 | Miller |
| 5,538,499 A | 7/1996 | Schwenn et al. |
| 6,302,858 B1 * | 10/2001 | DeToro et al. ................... 602/5 |
| 6,533,741 B1 | 3/2003 | Lee et al. |
| 7,083,583 B2 | 8/2006 | Opahle et al. |
| 7,841,998 B2 | 11/2010 | Pomeroy et al. |

(Continued)

FOREIGN PATENT DOCUMENTS

GB    445921 A * 4/1936 ............... A61F 5/01

*Primary Examiner* — Michael Brown
(74) *Attorney, Agent, or Firm* — Hauptman Ham, LLP

(57) ABSTRACT

An orthotic method for newborn babies includes the step of providing a newborn orthopedic device constructed and dimensioned to fit a newborn baby within hours of birth for a skeletal modification. The method also includes the step of conducting a thorough physical examination of a newborn baby for skeletal abnormalities by an orthopedic or medical professional. A newborn baby is fitted with an appropriate device to correct the prevailing skeletal abnormality and the device is adjusted to overcome the physical abnormality by an increment of one millimeter and allowed to remain in that position for 24 hours. Thereafter the method increases the bias by adjusting the orthopedic device by a movement of about one millimeter and applying the increased bias for about 24 hours before further adjustments in one millimeter increments each for about a 24 hour period.

3 Claims, 8 Drawing Sheets

(56) References Cited

U.S. PATENT DOCUMENTS

| | | |
|---|---|---|
| 7,988,652 B2 | 8/2011 | Chao |
| 8,251,934 B2 | 8/2012 | Bonutti |
| 2007/0027421 A1* | 2/2007 | Nobbe et al. .................. 602/27 |
| 2011/0040225 A1* | 2/2011 | Gibbons ............... A61F 5/0127 602/23 |
| 2012/0330204 A1 | 12/2012 | Baldauf et al. |

* cited by examiner

ORTHOTIC METHOD AND DEVICE FOR NEWBORN BABIES

FIELD OF THE INVENTION

This invention relates to orthotic methods and devices for newborn babies and more particularly to orthopedic devices for correcting skeletal abnormalities of the foot and toes of a newborn human being.

BACKGROUND FOR THE INVENTION

Some babies are born with skeletal abnormalities as for example in the hands, feet and in other important parts of the body such as a child's shoulders, arms, hands and fingers, their legs, knees and neck etc. In such cases, it is desirable to correct the abnormality by biasing a limb or appendage toward the correct position.

Corrections of skeletal abnormalities of important parts of the human body by orthopedic devices have been done for many years. For example, a Toe Straightening Device is disclosed in a U.S. Patent of Marcus that issued in 1962 U.S. Pat. No. 3,049,120. As disclosed therein, the device consists of a structure for the toe of a foot and particularly for the largest toe in order to reposition the toe into a normal position.

A more recent U.S. Patent of Dieterich U.S. Pat. No. 4,244,359 discloses an orthopedic sandal for the correction of hammer toes and Hallux Valgus (X-toe). The sandal includes a lever arm extending along the longitudinal axis of the sole of a sandal and being pivotally connected to the sole in its rearward portion. A toe holding bar for pressing the toes downward is connected to the free end of the lever arm and various embodiments of mechanisms for moving the large toe medially for correcting Hallux Valgus are operatively associated with the lever arm. Further mechanisms for stretching the large toe in conjunction with the intermittent treatment of the Hallux Valgus are operatively interconnected with the mechanisms for moving the large toe medially.

A much more recent U.S. Patent of Bonutti U.S. Pat. No. 8,251,934 relates to Orthosis and Method for Cervical Mobilization issued on Aug. 28, 2012. As disclosed a neck brace to move a neck of a person or stabilize the neck includes connecting a vest to the neck brace to a torso of a person. A support member of the neck brace is connected to the vest. A chin support of the neck brace is connected to a chin of the person. Force is applied between the support member and the chin support to move the chin support relative to the support member. A cam member of the neck brace guides movement of the chin support relative to the support member.

The above are examples of a plurality of patents directed to correcting abnormalities in the shoulder, arm, knee, foot and toes as well as hands and fingers. Nevertheless, to the best of Applicant's knowledge there are no presently available devices that are specifically designed for newborn human babies within a few hours of birth. It is now believed that applying specially designed orthopedic devices for human babies that are only a few hours old will provide a more immediate correction to such abnormalities. Accordingly, it is believed that there is a need including a demand on a commercial level for the devices and methods in accordance with the present invention.

BRIEF SUMMARY OF THE INVENTION

In essence the present invention contemplates an orthopedic device for correcting an abnormality of the foot and toes of a newborn baby. The orthopedic device comprises or consists of a sole member that is constructed and dimensioned to engage the bottom surface of patient's foot and toes. The sole member includes a rear portion that is fixed with respect to a lower leg and heel of the patient. The sole member also includes a front portion movably connected to the rear portion and five toe engaging compartments movably fixed to the front portion for biasing one or more toes in preselected directions. In addition, a soft skin engaging portion surrounds an upper portion of a patient's foot and toes, angles and lower portion of the patient's leg. Still further, a first pair of straps are provided for encircling a lower portion of the patient's leg and a pair of rods fix the rear portion of the sole member against a patient's heel and the first pair of straps. In addition, a second pair of straps fix the patient's foot to the forward portion of the sole member. Finally, an adjustment mechanism is provided for biasing the forward portion of a patient's foot and toes in an upwardly, downwardly and left or right direction.

In a further embodiment of the invention, an orthopedic method comprises or consists of the following steps.

a) Providing a newborn sized orthopedic device that is constructed and dimensioned to fit a newborn baby for skeletal modifications.

b) In a second step, a thorough physical examination for skeletal abnormalities is conducted on a newborn baby within hours of the baby's birth.

c) In a third step a newborn baby with a skeletal abnormality is fitted with an orthopedic device for correcting the skeletal abnormality.

d) In the next step the orthopedic device is adjusted to apply a bias toward correcting the physical abnormality.

e) In a final step the bias is increased by adjusting the orthopedic device in a one millimeter increment, leaving the adjusted bias for about 24 hours and repeating the final step until the abnormality is fully corrected.

The invention will now be described in connection with the accompanying drawings wherein like reference numerals have been used to identify like parts.

DETAILED DESCRIPTION OF THE PREFERRED EMBODIMENTS OF THE INVENTION

Figure 1:
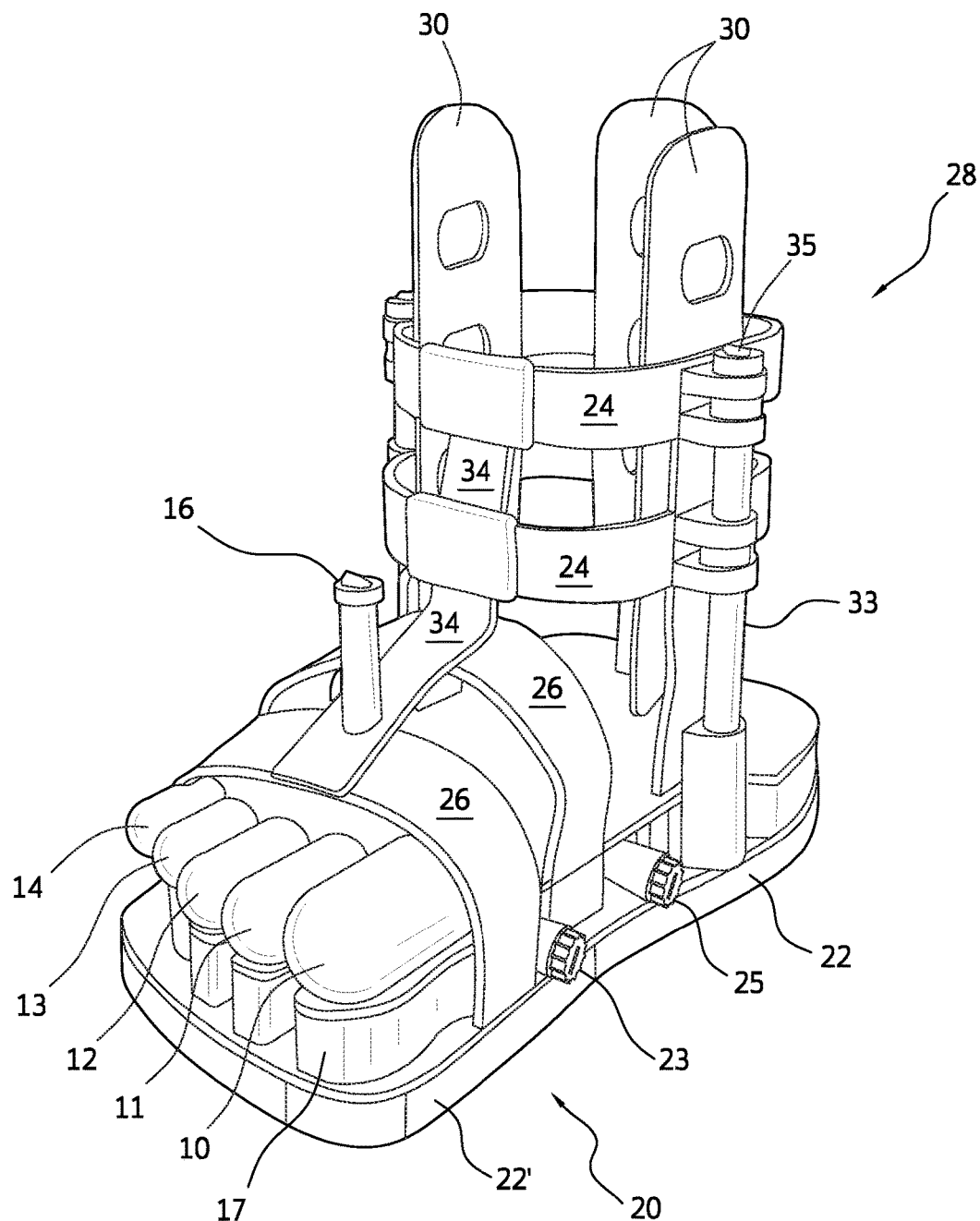
FIG. 1 is a perspective view of the structural elements of an orthopedic shoe in accordance with the present invention.
Figure 2:
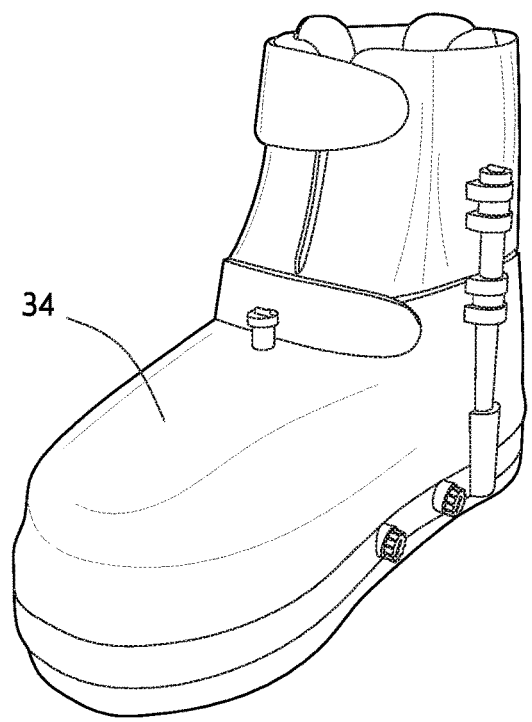
FIG. 2 is a perspective view of a finished shoe in accordance with the present invention.
Figure 3:
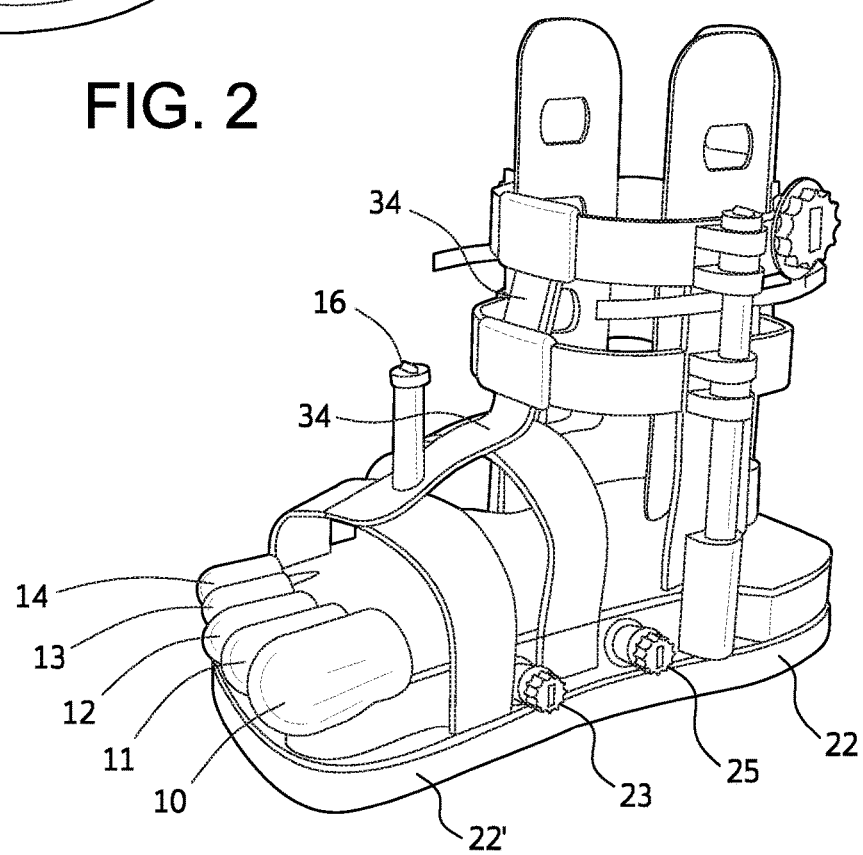
FIG. 3 is a schematic illustration with adjusted mechanisms for biasing a patient's toes in an upwardly and downwardly, to the left and to the right and the foot to the left or right.

Referring now to FIGS. 1-13 and more particularly to FIGS. 1 and 3, an orthopaedic shoe like adjustable brace is sized to fit a newborn baby from as early as one hour to within 10 or 12 hours of birth. Preferably, the adjustable orthopaedic device is fitted to the patient within six hours of birth and preferably at least within 10 to 12 hours of birth. It is desirable to apply the device as early as possible after a careful physical examination for skeletal abnormalities.

Figure 4:
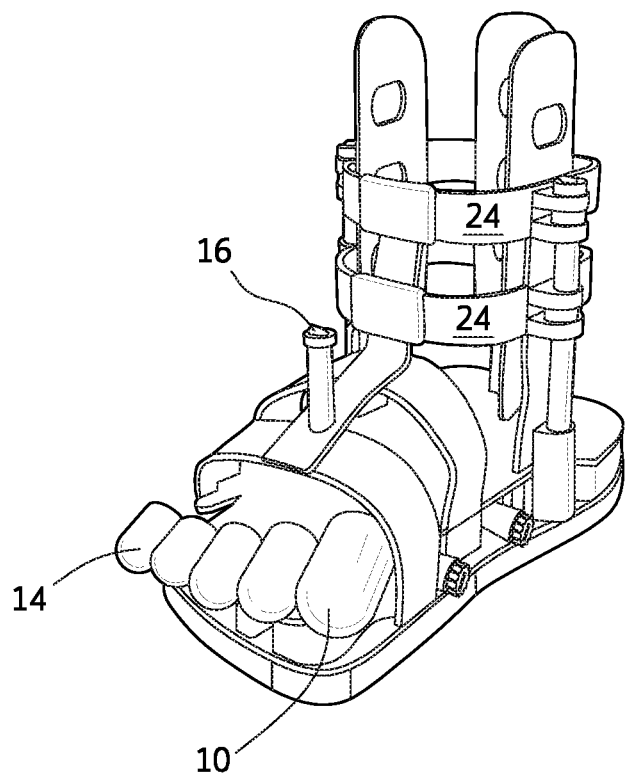
FIG. 4 is a schematic illustration of the structural elements of an orthopedic shoe shown in FIG. 3 but with the toe compartments oriented to the left.
Figure 6:
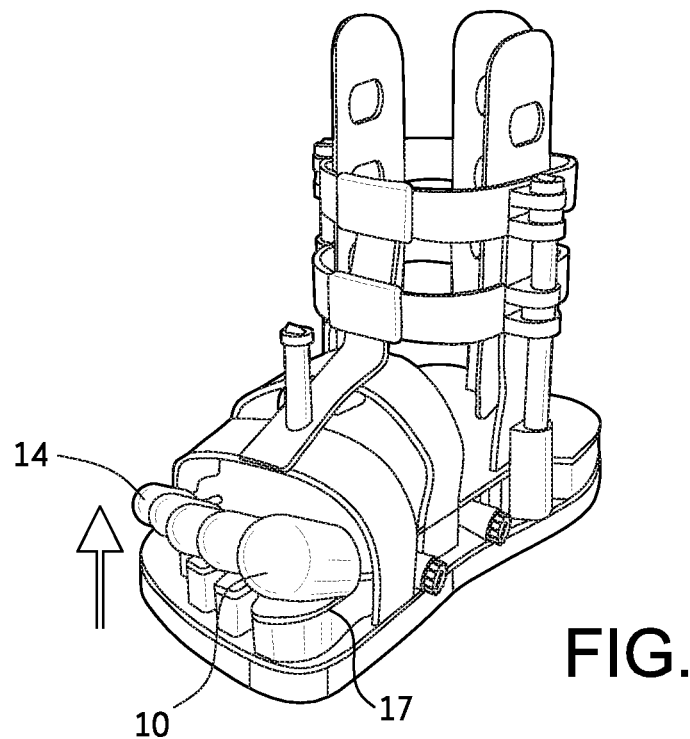
FIG. 6 is a schematic illustration of the structural elements of an orthopedic shoe shown in FIG. 5 but with the toe compartments oriented in an upward direction.
Figure 7:
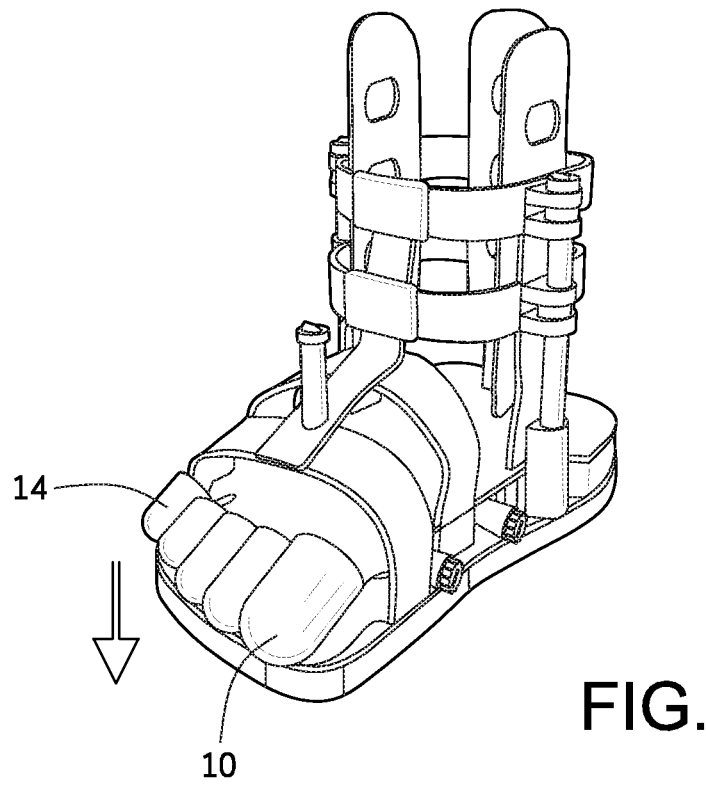
FIG. 7 is a schematic illustration of the structural elements of an orthopedic shoe shown in FIG. 6 but with the toe compartments oriented in a downward direction.
Figure 8:
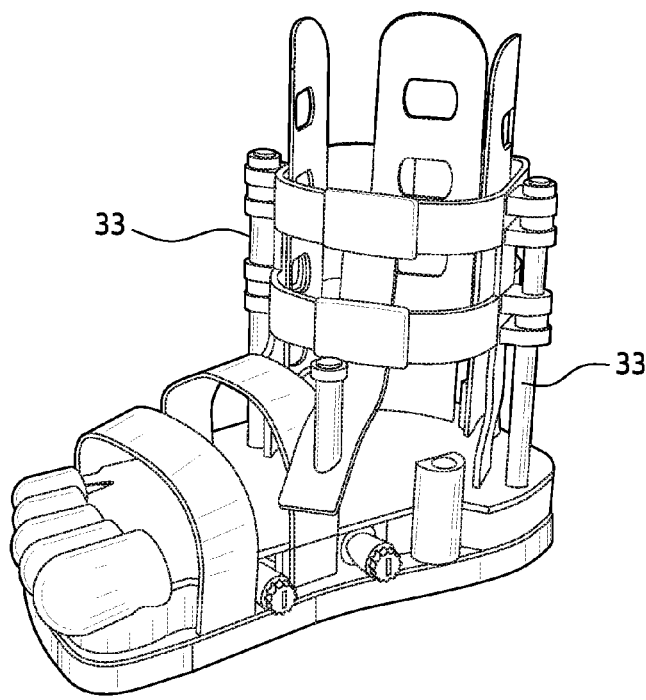
FIG. 8 is a schematic illustration of the structural elements of an orthopedic shoe shown in FIG. 7 but with the sole member rotated to the right with respect to the leg of a patient.
Figure 9:
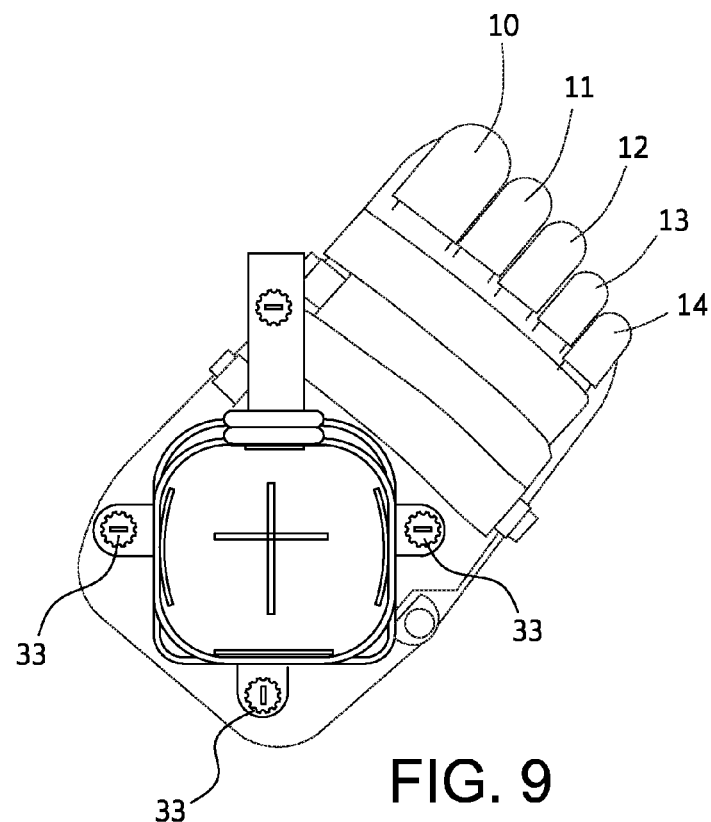
FIG. 9 is a schematic illustration of the structural elements wherein the sole member is rotated to the right with respect to a patient's leg.

As shown, an orthopaedic shoe like adjustable device 28 includes a sole member 20 having a rear portion 22 and a front portion 22'. The front portion 22' is movably connected to the rear portion 22 and is rotatable upwards and downwards with respect to the rear portion 22 about a hinge like adjustable connection. This rotation is illustration in FIGS. 7 and 8 wherein five toe engaging compartments 10, 11, 12, 13 and 14 are adapted to receive a single toe therein, as for example the largest toe in compartment 10 and the smallest toe in compartment 14. Toe adjustment may be made by knob 25. FIG. 4 illustrates toe movement to the left and FIG. 5, toe movement to the right. Further, FIG. 6 illustrates toe movement upwardly and FIG. 7 illustrates toe movement downwardly.

As illustrated in FIG. 2, the majority of the structural elements described are covered with a soft cloth skin engaging cover 34 or light foam that may be deployed on an inner side of the structural straps. It should be noted that all of the elements are of as light a weight as possible.

Figure 5:
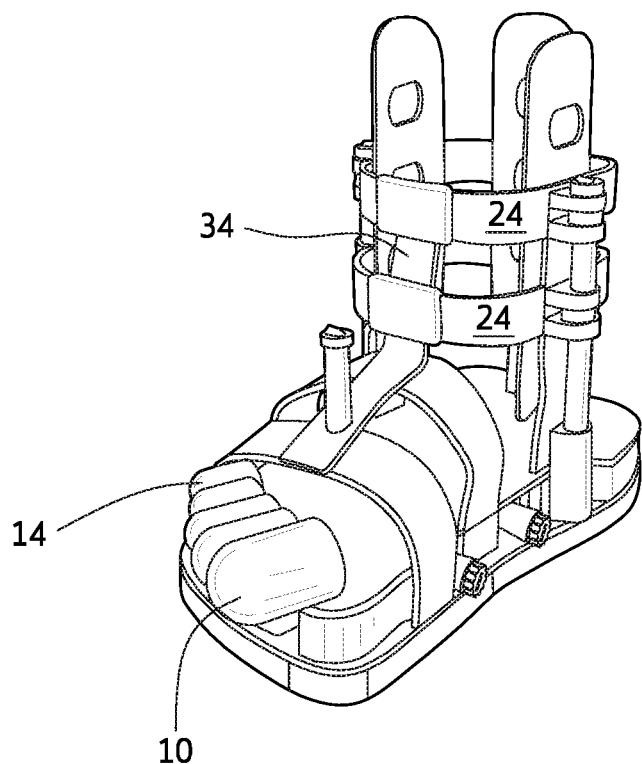
FIG. 5 is a schematic illustration of the structural elements of an orthopedic shoe shown in FIG. 4 but with the toe compartments oriented to the right.

An adjustment mechanism for an abnormality wherein the toes are directed to the left or the right are illustrated in FIGS. 4 and 5, respectively. As illustrated, in FIGS. 4, 5, 6 and 7 each of the toe engaging compartments receive a single toe therein and an adjustment by increasing the bias toward a normal or centered position by one millimeter increase and allowed to remain in that position for about 24 hours. These one millimeter increases are repeated each for 24 hour periods until the toes are positioned in the normal position. In this manner, the toes are repositioned to the left or right and/or in an upper or downward direction and are stabilized in the correct position by remaining in that position for about 48 hours.

The adjustable device also includes a first pair of straps 24 that encircle a lower portion of a patient's lower leg and ankle and a second pair of straps 26 that extend across the top of a patient's foot and are fixed on opposite sides thereof to the sole member 20. In addition, the device 28 includes three upwardly extending splints 30 that extend upwardly to a position along the lower leg slightly above the ankle. The three splints are located with one splint along the back of the patient's lower leg and one splint along each side of the patient's leg. Each of the splints includes a plurality of openings along the length of the splint.

Figure 10:
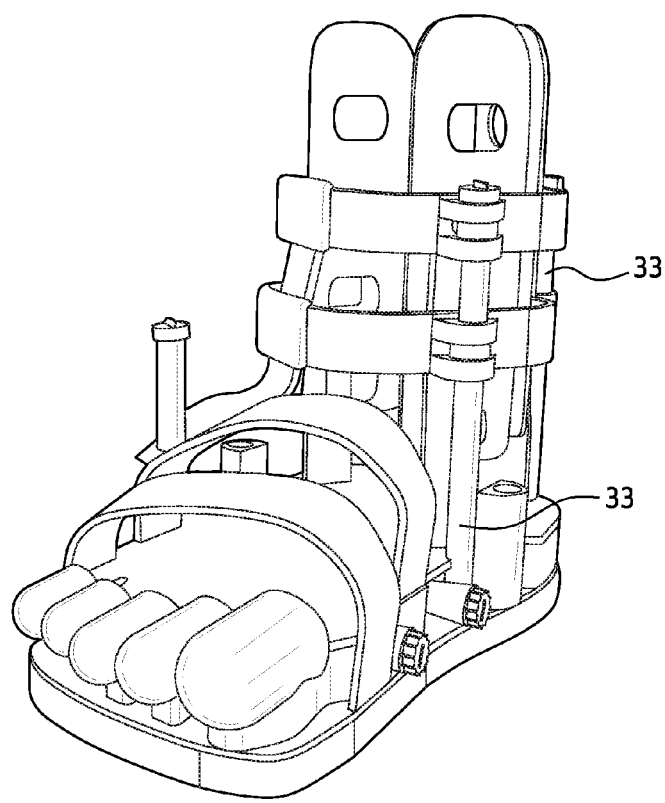
FIG. 10 is a schematic illustration of the structural elements of an orthopedic shoe shown in FIG. 9 but with the sole member rotated to the left.
Figure 11:
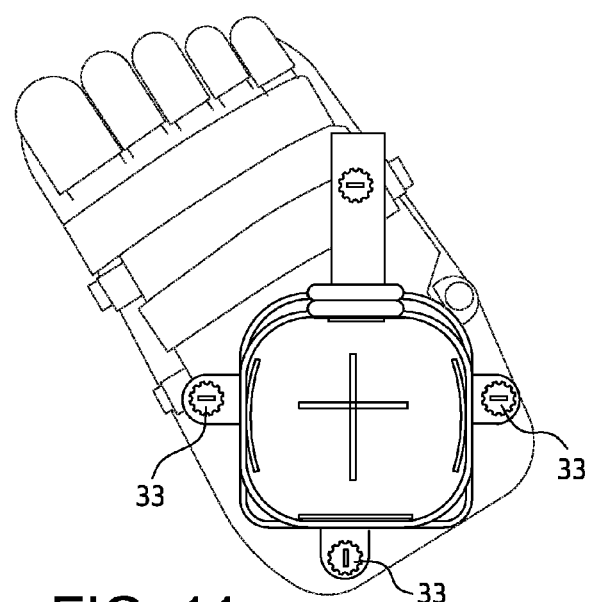
FIG. 11 is a schematic illustration of the structural elements looking down on the sole member as rotated to the left.
Figure 12:
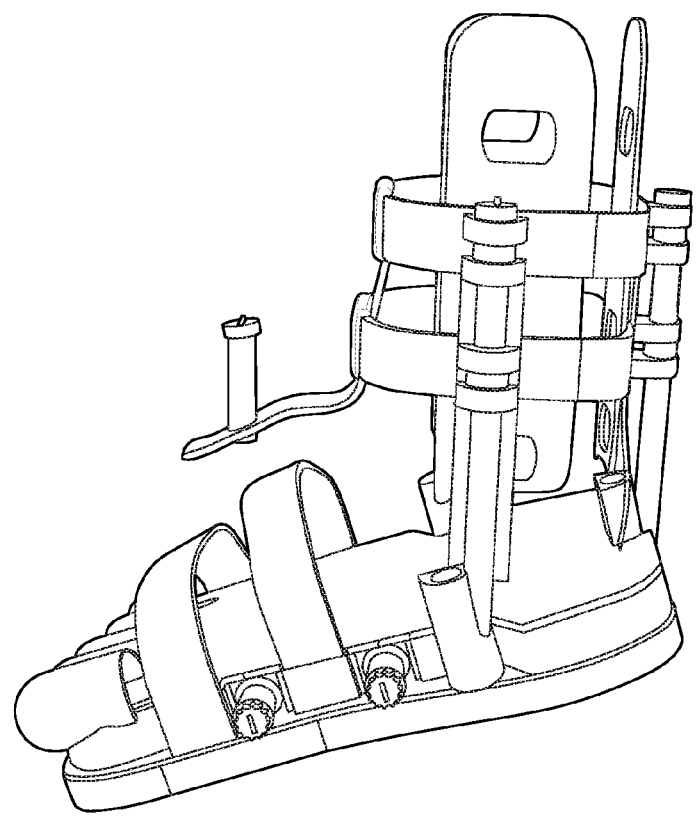
FIG. 12 is a schematic illustration of the structural elements of an orthopedic shoe shown in FIG. 3 but illustrating the rotation of the sole member in a downward direction.
Figure 13:
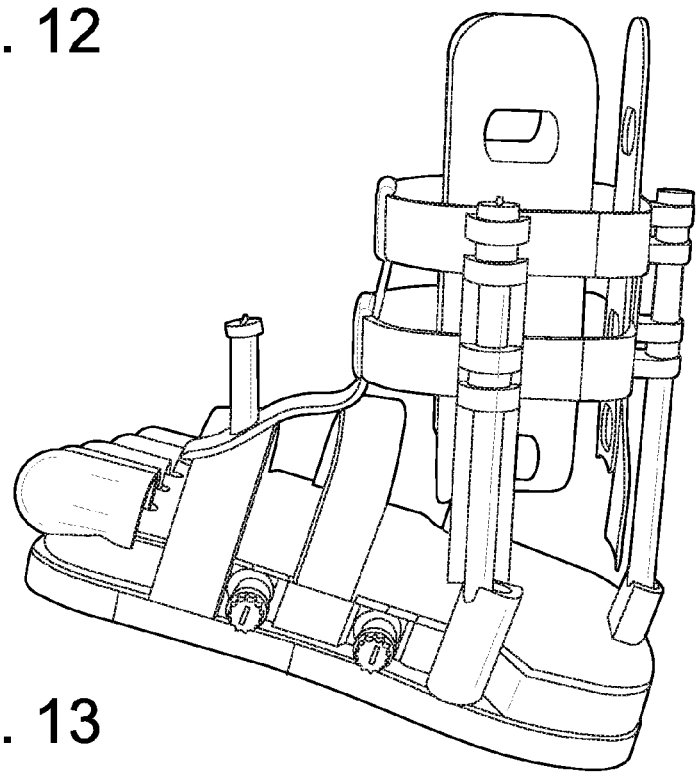
FIG. 13 is a schematic illustration of the structural elements of an orthopedic shoe as shown in FIG. 12 but with the sole member rotated in an upper position.

A fourth molded plastic splint extends from an upper portion of a patient's foot up through an upper strap 24. Further, the device 28 includes three rods 33 that fix the bottom of the patient's foot to a rear portion 22 of a sole member 20. The three rods 33 are generally parallel to the patient's lower leg bone and fixed to a base member that may be fixed with respect to the rear portion 22 or to allow for limited rotation as shown in FIGS. 10 and 12.

The present invention also contemplates an orthopaedic method for correcting a skeletal abnormality in a newborn baby within about one (1) hour to ten (10) or twelve (12) hours of the baby's birth. The method includes the steps of:

a) conducting a thorough physical examination of a newborn baby for skeletal abnormalities by an orthopaedic or medical professional;

b) providing a newborn sized orthopedic device selected from the group consisting of a shoe brace for correcting an abnormality of a foot and/or toes, a glove like orthopedic device for correcting abnormalities of the wrist, hand and fingers, a circular ring for supporting a patient's neck, a wrap for correcting an elbow, knee or wrist, and a shoulder supporting device anchored by cross straps, a wrap for an elbow, knee or wrist with supporting bars and a rotary device with adjustment means;

c) fitting a newborn baby with an appropriate orthopedic device selected from the group set forth in step b);

d) adjusting the device to apply a bias to overcome the physical abnormality by an increment of one (1) millimeter and leaving the adjustment for about 24 hours; and e) increasing the bias repeatedly by increments of 1 mm, applying the bias for about 24 hours before further adjustments of 1 mm increments until a normal position is achieved and allowing the normal position to stabilize.

Figure 14:
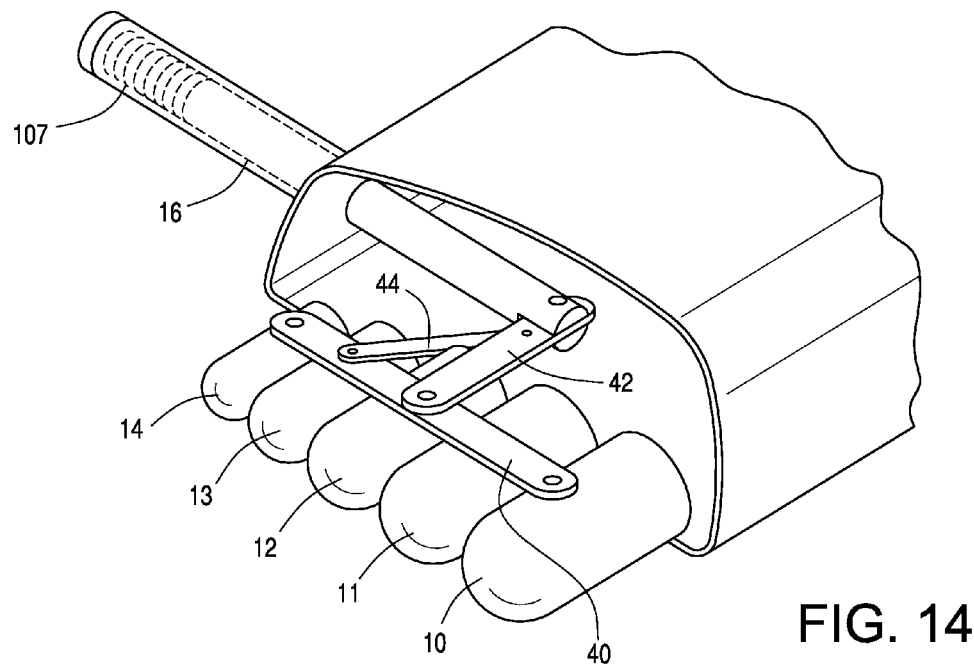
FIG. 14 is a schematic illustration of a mechanism for biasing the toes to the left or right as indicated in FIGS. 4 and 5.

As illustrated in FIG. 14, a mechanism for biasing the toes of a newborn baby to the left or right includes five toe engaging compartments 10, 11, 12, 13 and 14 and a first connecting rod 40 such as a strip of metal plate that is rotatably connected to each of the toe engaging compartments 10, 11, 12, 13 and 14 as shown. A second connecting rod 42 is directed from the first connecting rod 40 and rotatably connected at one end thereof to the middle of the rod 40. As shown a rotatable connection passes through the rod 40 and the toe engaging rotatable connection to the middle toe.

A third connecting rod 44 is diagonally directed from about the middle of the second connecting rod 42 to the first connecting rod 40 at or about the fourth toe engaging compartment 13. The second and third connecting rods 42 and 44 like the first connecting rod 40 are preferably in the form of a generally flat metal plate and generally rotatably connected to one another. As constructed or connected the second connecting rod 42 is rotatably connected to the first connecting rod at about the middle of the first connecting rod 40 and also to the toe engaging compartments 10-14. An activator rod 16 or adjuster includes a first threaded end 107 that is operatively connected to a watch like dial (not shown) that will move the toes left or right in one millimeter directions.

Figure 15:
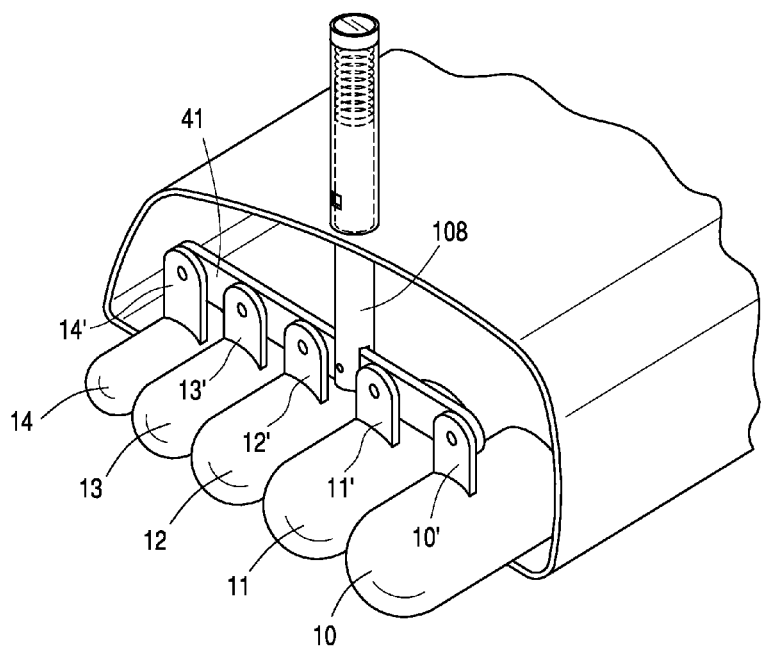
FIG. 15 is a schematic illustration of a mechanism for biasing the toes upwardly or downwardly as indicated in FIGS. 6 and 7.

A mechanism for biasing a patient's toes in an upward and downward direction is illustrated in FIG. 15. As shown, the mechanism includes a plurality of toe engaging compartments 10, 11, 12, 13 and 14 each of which includes a relatively short upwardly extending connecting stub 10', 11', 12', 13' and 14'. Each of the connecting stubs 10'-14' is connected to a crossbar 41 that is connected to an adjustment mechanism 108. As illustrated, the crossbar is moved upwardly or downwardly by rotation of a knob at the top of the mechanism 108 to lift each of the toe compartments 10-14 to thereby bias the toes in an upward or downward direction. In a preferred embodiment of the invention, a more complex but similar upward and downward mechanism may include a lower adjuster 17 that elevates and lowers the toe compartments that are attached to the sole member 20.

In the preferred embodiment of the invention the method comprises or consists of the following steps while a further preferred embodiment of the invention the steps consists of selecting a newborn sized orthopaedic device for correcting for abnormalities in the foot and/or toes.

While the invention has been described in connection with the above-identified preferred embodiments, it should be recognized and understood that changes and modifications may be made therein without departing from the scope of the appended claims.

What is claimed is:

1. An orthopedic device for correcting a disability of the foot and/or toes of a newborn baby, said device consisting of:
   a sole member constructed and dimensioned and adapted to engage a bottom surface of a newborn baby's foot and toes, said sole member fixed with respect to a newborn baby's lower leg and heel and a front portion movably connected to said rear portion, five toe engaging members movably fixed to said front portion for biasing said toes in preselected directions, a first pair of leg encircling straps and a pair of vertical rods adapted for fixing the newborn baby's heel and ankle to said fixed rear portion of said sole member and a second pair of straps extending across an upper portion of the newborn baby's foot where the ends of each of said second pair of straps fixed to said forward portion of said sole member and means for adjusting said forward portion of said sole member to bring said foot and toes in an upward or downward or to the right or left directions in one millimeter increments for periods of 24 hours.

2. An orthopedic device for correcting a disability of the foot and/or toes of a newborn baby, said device consisting of a sole member constructed and dimensioned to engage the bottom surface of a newborn baby's foot and toes, said sole member including a rear portion fixed with respect to a lower leg and heel of the newborn baby and a front portion movably connected to said rear portion, five toe engaging movable members movably fixed to said front portion for biasing said toes in preselected directions, a soft portion surrounding an upper portion of the newborn baby's foot and ankle including a pair of straps for encircling a lower portion of the newborn baby's leg and a pair of vertical rods adapted for fixing said rear portion of said sole member against the newborn baby's heel and a second pair of straps encircling an upper portion of said foot connected to a forward portion of said sole member and means for biasing a forward portion of said sole member in an upward or downward direction in one millimeter increments.

3. An orthopedic method for newborn babies comprising the steps of:
   a) providing a newborn sized orthopedic device constructed and dimensioned to fit a newborn baby within hours of birth for skeletal modification;
   b) conducting a thorough physical examination of a newborn baby for skeletal abnormalities;
   c) fitting the newborn baby with a device to correct a skeletal abnormality;
   d) adjusting the device to apply a slight bias to overcome the physical abnormality; and
   e) increasing the bias by adjusting the orthopedic device by a movement of about one millimeter and applying the increased bias for about 24 hours before further adjustment in one millimeter increments each for about a 24 hour period.

* * * * *